United States Patent
Weber et al.

(10) Patent No.: US 11,937,789 B2
(45) Date of Patent: Mar. 26, 2024

(54) DEVICE AND METHOD FOR HEMORRHOID TREATMENT VIA RECTUM EXPANSION AND SPECIFIC SPECTRAL ILLUMINATION

(71) Applicant: Boston Scientific Scimed, Inc., Maple Grove, MN (US)

(72) Inventors: Jan Weber, Maastricht (NL); Nora Belkhayat, Framingham, MA (US); Hannah Rebar, Boston, MA (US); Nathan Thomas Cummings, Worcester, MA (US); Jessica Powers, Boston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 433 days.

(21) Appl. No.: 16/934,744

(22) Filed: Jul. 21, 2020

(65) Prior Publication Data

US 2021/0022595 A1 Jan. 28, 2021

Related U.S. Application Data

(60) Provisional application No. 62/877,023, filed on Jul. 22, 2019.

(51) Int. Cl.
*A61B 1/31* (2006.01)
*A61B 1/00* (2006.01)
(Continued)

(52) U.S. Cl.
CPC ............ *A61B 1/31* (2013.01); *A61B 1/00066* (2013.01); *A61B 1/00082* (2013.01); *A61B 1/0017* (2013.01); *A61B 1/0676* (2013.01); *A61B 1/0684* (2013.01); *A61B 1/32* (2013.01); *A61B 17/12013* (2013.01); *A61M 29/02* (2013.01);
(Continued)

(58) Field of Classification Search
CPC ......... A61B 1/31; A61B 1/00; A61B 1/00082; A61B 1/00066; A61B 1/06; A61B 1/0684; A61B 1/0017; A61B 17/12; A61B 17/1201
See application file for complete search history.

(56) References Cited

U.S. PATENT DOCUMENTS 6,077,257 A 6/2000 Edwards et al.
6,755,849 B1 6/2004 Gowda et al.
(Continued)

FOREIGN PATENT DOCUMENTS

CN 104507380 4/2015
GB 2408209 5/2005

OTHER PUBLICATIONS

Yokota et al., "Ultraflexible organic photonic skin"; Science Advances, Apr. 15, 2016, 8 sheets.

*Primary Examiner* — Christopher J Beccia
(74) *Attorney, Agent, or Firm* — Fay Kaplun & Marcin, LLP (57) ABSTRACT

A device includes a balloon configured for inflation with a light-diffusing fluid and configured, upon inflation, to expand a body lumen within which it is positioned and a flexible light-emitting device attached to the balloon having a light-emitting side facing radially inward toward the fluid so that, during a medical procedure, light emitted from the light-emitting side is diffused by the fluid and illuminates a treatment area within the body lumen proximal to the balloon.

19 Claims, 8 Drawing Sheets

(51) Int. Cl.
- *A61B 1/06* (2006.01)
- *A61B 1/32* (2006.01)
- *A61B 17/12* (2006.01)
- *A61M 29/02* (2006.01)
- *A61B 17/00* (2006.01)
- *A61B 17/34* (2006.01)
- *A61B 90/30* (2016.01)

(52) U.S. Cl.
CPC ............... *A61B 2017/00557* (2013.01); *A61B 2017/00818* (2013.01); *A61B 2017/12018* (2013.01); *A61B 2017/3452* (2013.01); *A61B 2017/3486* (2013.01); *A61B 2090/306* (2016.02); *A61B 2090/309* (2016.02)

(56) References Cited

U.S. PATENT DOCUMENTS

| | | | |
|---|---|---|---|
| 7,252,667 B2 | 8/2007 | Moses et al. | |
| 8,801,699 B2* | 8/2014 | Kalser | A61M 25/0017 |
| | | | 604/96.01 |
| 9,808,179 B2* | 11/2017 | O'Dea | A61M 25/1018 |
| 2013/0035556 A1 | 2/2013 | Kalser et al. | |
| 2014/0058271 A1* | 2/2014 | Ryan | A61B 5/0071 |
| | | | 600/477 |
| 2016/0151638 A1* | 6/2016 | McCormack | A61N 5/0601 |
| | | | 604/20 |
| 2019/0099186 A1 | 4/2019 | Piskun | |

* cited by examiner

DEVICE AND METHOD FOR HEMORRHOID TREATMENT VIA RECTUM EXPANSION AND SPECIFIC SPECTRAL ILLUMINATION

PRIORITY CLAIM

The present disclosure claims priority to U.S. Provisional Patent Application Ser. No. 62/877,023 filed Jul. 22, 2019; the disclosure of which is incorporated herewith by reference.

FIELD

The present disclosure relates to the treatment of hemorrhoids and, in particular, relates to a device and a method for hemorrhoid treatment via rectum expansion and specific spectral illumination.

BACKGROUND

Hemorrhoids are swollen and inflamed blood vessels around the anus or in the lower rectum. Hemorrhoids may be external, forming under the skin around the anus, or internal, forming in the lining of the anus and the lower rectum. Approximately 50% of adults older than 50 years of age in the United States have experienced symptoms, including bleeding, irritation or pain, due to hemorrhoids.

A method for treating hemorrhoids is ligation banding. Hemorrhoids swell directly after being banded and protrude away from the wall of the anus/rectum. When hemorrhoid cases involve multiple hemorrhoids, additional swelling may cause the already banded hemorrhoids to block the free space necessary to treat subsequent hemorrhoids. The treating physician may have difficulty maneuvering the banding device to locate subsequent hemorrhoids after the initial hemorrhoids have been banded. In such cases, the patient must wait for the treated hemorrhoid(s) to shrink or disappear before returning for subsequent treatments.

Another method for treating hemorrhoid is sclerotherapy, where a proctoscope is used to examine the anal cavity, rectum or sigmoid colon and a liquid containing drugs such as quinine, polidocanol or zinc chloride is injected into the area around any enlarged hemorrhoids. The drug injection may reduce the blood supply to the tissue to shrink the hemorrhoids. The proctoscope has a light for aiding the inspection of the membranes lining the anus. Conventional white light may allow for the identification of veins in the area of the hemorrhoids, however, locating the veins may be a difficult task when the veins are deeper in the tissue.

SUMMARY

The present disclosure relates to a device includes a balloon configured for inflation with a light-diffusing fluid and configured, upon inflation, to expand a body lumen within which it is positioned; and a flexible light-emitting device attached to the balloon having a light-emitting side facing radially inward toward the fluid so that, during a medical procedure, light emitted from the light-emitting side is diffused by the fluid and illuminates a treatment area within the body lumen proximal to the balloon.

In an embodiment, the device further includes an inner member affixed to the balloon extending from a proximal end of the balloon to a distal end of the balloon; and an outer tube affixed to the proximal end of the balloon and extending to a fluid source.

In an embodiment, the inner member is a rod or a tube.

In an embodiment, the device further includes an anchor plate comprising an affixation location for the outer tube, the anchor plate preventing the balloon from migrating during the medical procedure.

In an embodiment, the light-emitting device is an OLED foil.

In an embodiment, the OLED foil has power terminals and wiring extending from the power terminals through the inner member to a power source.

In an embodiment, the light-emitting device comprises at least one optical fiber embedded in a surface of the balloon.

In an embodiment, a distribution of a spectrum in the visible light range is modifiable to adjust a frequency and an intensity of the light emitted from the light-emitting device.

In an embodiment, the balloon is one of non-compliant or semi-compliant.

The present disclosure also relates to a device includes a balloon configured for inflation with a light-diffusing fluid and configured, upon inflation, to expand a body lumen within which it is positioned; and a light-emitting device attached to the balloon and emitting light directed so that, when the device is in a desired position within a living body, the light passes through the light-diffusing fluid toward a treatment area within the body lumen proximal to the balloon.

In an embodiment, the light-emitting device is interior to the balloon and extends from a proximal end of the balloon to a distal end of the balloon, the light-emitting device emitting light radially outward through the light-diffusing fluid.

In an embodiment, the device further an inner tube attached to the balloon and extending from a proximal end of the balloon to a distal end of the balloon, wherein the light-emitting device is in the interior of the inner tube.

In an embodiment, the light-emitting device is an optical fiber.

In an embodiment, the light-emitting device is an OLED foil.

In an embodiment, a distribution of a spectrum in the visible light range is modifiable to adjust a frequency and an intensity of the light emitted from the light-emitting device In addition, the present disclosure relates to a method including inserting a device into a body lumen of a living body, the device comprising a balloon inflatable with a light-diffusing fluid and a flexible light-emitting device having a light-emitting side facing radially inward toward the fluid; and inflating the balloon with the light-diffusing fluid so that light emitted from the light-emitting side is diffused by the fluid and illuminates a treatment area within the body lumen proximal to the balloon.

In an embodiment, the light-emitting device is an OLED foil

In an embodiment, the OLED foil has power terminals and wiring extending from the power terminals through an inner member to a power source.

In an embodiment, the light-emitting device comprises at least one optical fiber embedded in a surface of the balloon.

In an embodiment, a distribution of a spectrum in the visible light range is modifiable to adjust a frequency and an intensity of the light emitted from the light-emitting device.

BRIEF DESCRIPTION

DETAILED DESCRIPTION

The present disclosure may be further understood with reference to the following description and the appended drawings, wherein like elements are referred with the same reference numerals. The present embodiments are directed to a balloon device having a light-emitting feature and a method for implementing the balloon device in a hemorrhoid treatment procedure. The balloon device may be inflated within the rectum and illuminated to diffuse light over a hemorrhoid treatment area. In one embodiment the light-emitting feature is an ultraflexible OLED foil. The technology to produce such a foil is described, for example, in "Ultraflexible organic photonic skin" by Yokota et al., Science Advances, published 15 Apr. 2016, to be described in detail below. In another embodiment the light-emitting feature is a flexible side-emitting optical fiber, which will also be described in detail below. In another embodiment the light-emitting feature uses fluorescence.

The balloon device of this embodiment is insertable in the rectum and inflated with a fluid (liquid or gas) such as, for example, a sterile saline solution or air, so that the increase in the size of the balloon device stretches the rectum and, indirectly, the anus. The balloon device is illuminated by the light-emitting feature to enhance the visibility of the hemorrhoid treatment area. For example, fluorescence may be used as the light-emitting feature either as fluorescence dye in the fluid inside of the balloon device or as a coating on the balloon device surface. In the above-mentioned embodiments the light-emitting feature has an adjustable frequency band to change a color and intensity of the emitted light. The physician may modulate the frequency band to optimize the visibility of the hemorrhoidal tissue.

Figure 1:
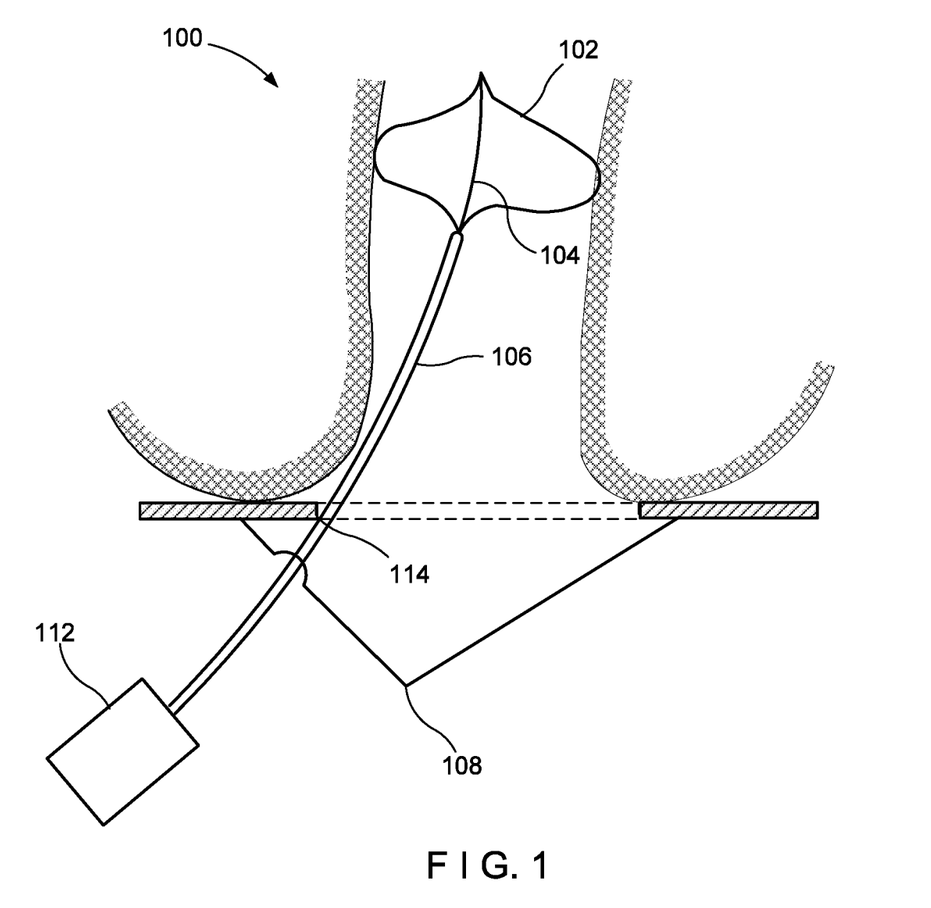
FIG. 1 shows a balloon device for expanding and illuminating a hemorrhoid treatment area according to various exemplary embodiments of the present disclosure.

To locate veins, it is advantageous to use light within a spectral range that penetrates tissue, is absorbable by hemoglobin, and is visible to the human eye. Human skin typically reflects short-wavelength light (e.g., blue and green) and absorbs long-wavelength light (e.g., orange and red). The intensity of the light reflected from the surface of the skin may overpower the transmitted light, limiting the visualization of veins. Reflected light is reduced and deeper veins visualization is increased by applying LED light waves, which are easily absorbed by deoxygenated hemoglobin in venous blood and show up as dark areas on the skin FIG. 1 shows a balloon device 100 including a balloon 102, an inner member 104 and an outer tube 106. The inner member 104 is bonded to the interior of the balloon 102 at the proximal and distal ends of the balloon 102, similarly to a vascular balloon as would be understood by those skilled in the art. In some embodiments, the inner member may be attached to the interior of the balloon 102 using some other attachment mechanism. The balloon 102 of this embodiment may, for example, be non-compliant or semi-compliant to inflate into a predetermined shape as the balloon 102 is inflated without substantial stretching of the material from its uninflated state. However, in some embodiments, a compliant balloon may be used. The balloon 102 may be formed of, e.g., a synthetic polymer such as polyamide, polyurethane or silicone. The balloon is preferably transparent or substantially transparent.

The inner member 104 limits the longitudinal elongation and compression of the balloon 102. In other words, the balloon 102 has a proximal/distal length that is substantially constant regardless of whether the balloon 102 is fully inflated, fully deflated, or in an intermediate state. Similar to a vascular balloon, the inner member 104 may be a tube. However, because the balloon device 100 need not feed fluids from one end of the device 100 to the other end, the inner member 104 may be a rod, or a tube carrying a light-emitting feature in its lumen, as explained in further detail below. The inner member 104 may be a polymer or, if the inner member 104 is a rod, the rod may be metal. If the inner member 104 is a metal rod it may have a smaller cross-section than a polymer rod or tube. The inner member 104 may be transparent, particularly when the inner member 104 is a tube with a light-emitting feature in its lumen. The inner member 104 may extend out the proximal end of the balloon 102 and down the interior of all or part of the outer tube 106, or, as shown in the present embodiment, may extend only between the proximal and distal ends of the balloon 102.

The outer tube 106 extends from the proximal end of the balloon 102 to a pressurized fluid source and an optional balloon control apparatus 112 controlling the flow of fluids into and out of the balloon 102. The balloon 102 is generally inserted into the rectum in a deflated state and inflated with the fluid via the outer tube 106 after insertion to expand the rectum during the hemorrhoid treatment procedure. Once the procedure has been completed, the balloon 102 may be deflated via the outer tube 106 and removed from the rectum in the deflated state. The optional balloon control apparatus 112 may inflate the balloon to a predefined pressure, or the operating physician may control the fluid flow and inflated pressure manually as would be understood by those skilled in the art.

The outer tube 106 of this embodiment is affixed to an optional anchor plate 108 that remains external to the patient during the treatment procedure. The anchor plate 108 may be ring-shaped, having an inner diameter large enough to allow access to the rectum by treatment tools and having an outer diameter large enough such that the anchor plate 108 may not slide into the anus or rectum when the balloon 102 is in the inflated state. An affixation point 114 on the anchor plate 108 prevents the balloon 102 from migrating proximally or distally after a proper location for the balloon 102 in the rectum has been established. For example, the affixation point 114 may have a releasable clamp. When the clamp is released, the outer tube 106 and the balloon 102 may freely slide proximally and distally relative to one another. When the clamp is secured, the outer tube 106 and the balloon 102 are fixed at their current proximal-distal location relative to one another. However, other affixation means may be used. Thus, it may be seen that the location of the balloon 102 is adjustable to fit the patient anatomy yet fixable to prevent unwanted motion during the treatment procedure.

Figure 2A:
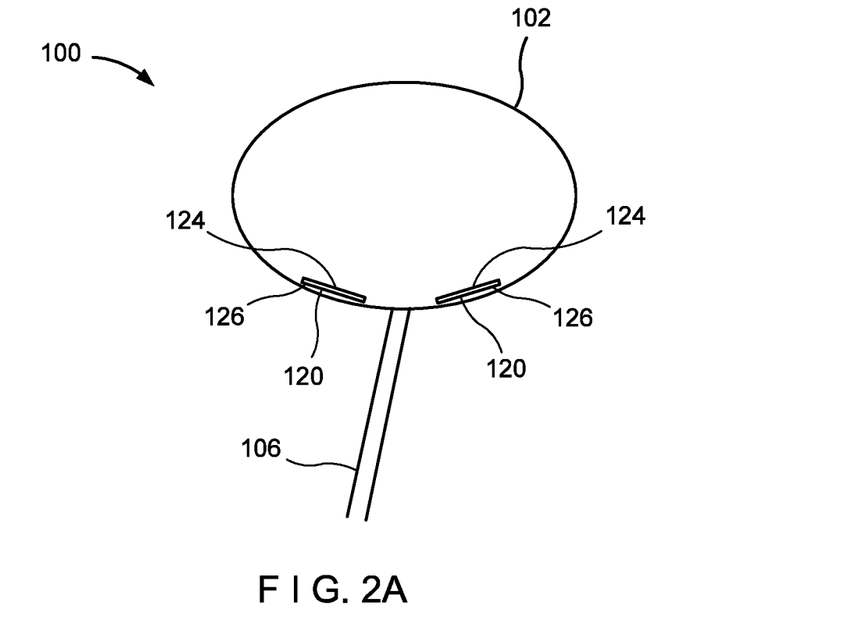
FIG. 2A shows the balloon device of FIG. 1 with an OLED foil as the light-emitting feature.
Figure 2B:
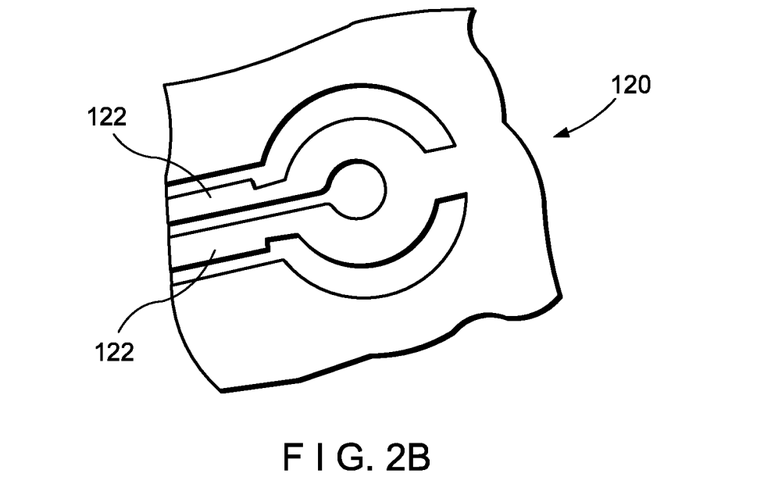
FIG. 2B shows the OLED foil of FIG. 2A.
Figure 3A:
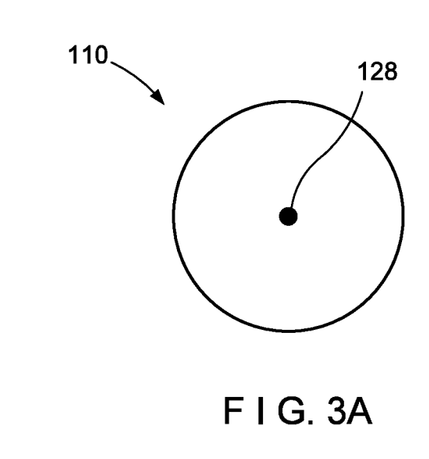
FIG. 3A shows a cross-section of a light-diffusing optical fiber, having a single core fiber, for use as the light-emitting feature in the balloon device of FIG. 1.
Figure 3B:
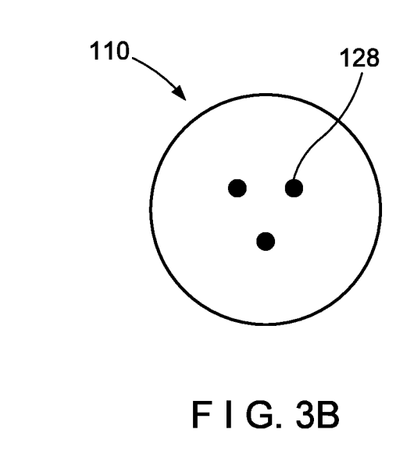
FIG. 3B shows a cross-section of a light-diffusing optical fiber, having a 3-core fiber, for use as the light-emitting feature in the balloon device of FIG. 1.
Figure 3C:
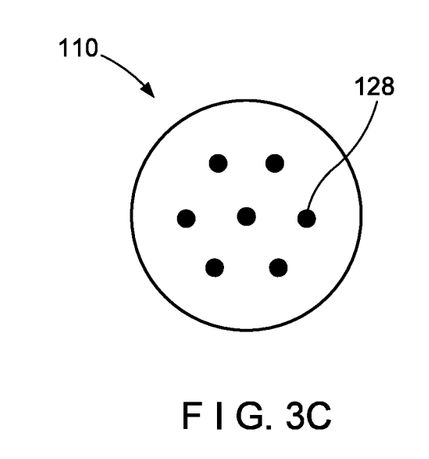
FIG. 3C shows a cross-section of a light-diffusing optical fiber, having a 7-core fiber, for use as the light-emitting feature in the balloon device of FIG. 1.
Figure 3D:
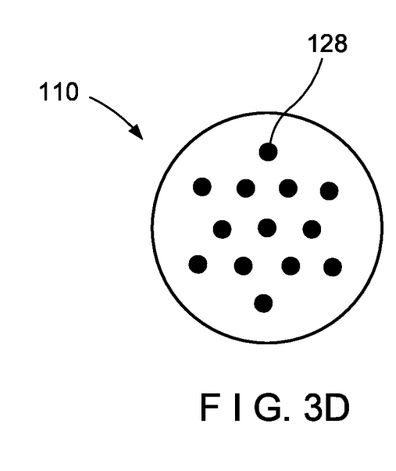
FIG. 3D shows a cross-section of a light-diffusing optical fiber, having a 13-core fiber, for use as the light-emitting feature in the balloon device of FIG. 1.
Figure 3E:
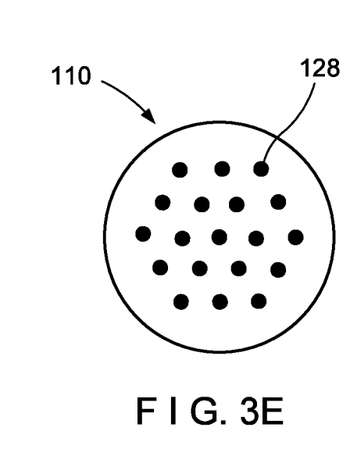
FIG. 3E shows a cross-section of a light-diffusing optical fiber, having a 19-core fiber, for use as the light-emitting feature in the balloon device of FIG. 1.

FIGS. 2A and 2B show the balloon device 100 of FIG. 1 including at least one flexible OLED foil 120 attached to the balloon. The balloon 102 is substantially transparent to allow the passage of light therethrough. The balloon 102 may, for example, be formed of a transparent polymer material such as polyamide or polyurethane. The OLED foil 120 is an ultrathin and ultra-flexible foil with a top and a bottom, the top being a light-emitting side 124 and the bottom being a non-light-emitting side 126. The foil 120 may be attached to the exterior or the interior of the balloon 102 at any location on the surface of the balloon 102. The foil 120 may be laminated or bonded to the balloon 102 to provide a protective layer from external elements that could damage the foil 120. However, an interior attachment provides further protection of the foil 120 to minimize or reduce potential damage during a procedure. In the embodiment shown in FIG. 2A, the balloon device 100 has two foils 120 attached to the interior of the proximal end of the balloon 102 with the light-emitting side 124 facing distally to illuminate the interior of the balloon 102. In a further embodiment, the foil 120 may be free floating in the interior of the balloon 102.

In the embodiment of FIG. 2B, the OLED foil 120 has power terminals 122 to which electric power is applied from an external source via suitable wiring running from the source to the power terminals 122. The foil 120 may be wired in multiple ways. When the foil 120 is interior to the balloon 102 it may be attached adjacent to the inner member 104 and power cabling may be run through the inner member 104, particularly when the inner member 104 is a tube, or along the inner member 104, particularly when the inner member 104 is a rod. In an alternate embodiment, wiring may be printed to the interior of the balloon 102 and/or the inner member 104. When the foil 120 is exterior to the balloon 102 the wiring may be similarly printed to the exterior of the balloon 102 and run down the outer tubing 106. In a further embodiment, the electrical connection may be made via printed traces running on the interior or exterior of the balloon 102 and/or on the outer tubing 106 or inner member 104.

The foil 120 is attached to the balloon 102 such that the light-emitting side 124 of the foil 120 is directed radially inward toward the interior of the balloon 102. For example, if the foil 120 is attached to the exterior of the balloon 102 the light-emitting side 124 will be adjacent to the surface of the balloon 102, and when the foil 120 is attached to the interior of the balloon 102 the non-light-emitting side 126 will be adjacent to the surface of the balloon 102. When the balloon 102 is inflated the fluid will scatter the light from the foil 120. When the fluid is e.g. water or saline an attachment point for the foil 120 toward the distal end of the balloon 102 may be preferable. In an alternate embodiment, where the fluid is a transparent or translucent milky solution such as e.g. milk or a calcium solution, an attachment point for the foil 120 toward the proximal end of the balloon 102 may provide substantially similar anatomy illumination as an attachment point toward the distal end. The milky solution scatters light passed into the balloon 102 to provide substantially homogeneous illumination to the treatment area.

The OLED foil 120 has a plurality of organic and inorganic layers. An active (organic) layer is formed as a bioluminescent layer comprising organic light-emitting materials. The active layer may, for example, include organic materials in a polymerized system (i.e., a PLED) having properties that cause the emission of light when voltage is applied thereto as would be understood by those skilled in the art. For example, blue PLEDs may use fluorescent emitters, whereas green and red PLEDs may use phosphorescent emitters. The OLED foil 120 may have a combination of red, blue and green light emission. The voltage applied to the foil 120 determines the frequency of the radiation emitted from the device.

The red, blue and green OLEDs will emit light at varying intensities depending on the frequency. As would be understood by those skilled in the art, the color and intensity of the light provided by the foil 120 are dependent on the voltage applied to the power terminals 122 and may be controlled via actuators located, for example, on a handle (not pictured) that remains external to the body. The color and intensity of the light given off by the foil 120 may be controlled during the treatment procedure to amplify the visibility of the treatment area. The foil 120 may be the ultraflexible OLED foil described in Yokota et al., however, the exemplary embodiments are not limited to the specific materials described therein.

In one embodiment the foil 120 is placed on a distal portion of the balloon 102 with the light-emitting side 124 of the foil 120 facing proximally toward an interior of the balloon 102. In this way, the light-emitting side 124 of the foil 120 faces a hemorrhoid treatment area proximal of the balloon 102 so that light is provided to the hemorrhoid treatment area after it has passed through the light-diffusing fluid within the balloon 102. The fluid diffuses the light to spread the supplied light substantially evenly throughout the treatment area. The flexibility of the foil 120 allows the foil 120 to go from a constricted/bent state on the deflated balloon 102 to an expanded state on the inflated balloon 102 while remaining attached to the balloon 102 and operable to emit light.

In an alternative embodiment, the foil 120 is attached directly to the inner member 104. For example, the inner member 104 may be a flexible metal rod and the foil 120 may be wrapped around the exterior of the member 104 with the light-emitting side 124 facing radially outward.

As discussed previously, as an alternative to the OLED foil 120, the balloon device may use a light-diffusing optical fiber 110 as the light-emitting feature (see FIGS. 3A-3E). Side-emitting optical fibers are flexible linear illuminators designed to promote leakage of the core-transmitted radiation via their side surfaces. The leakage can be achieved for example by adding specific scatters or fluorescent additives into the fiber core or cladding material or creating asymmetries in the fiber core/cladding geometry.

For example, fibers could be made by co-compounding nano-fillers such as TiO2 or ZnO2 into a core made out of Polymethyl-methacrylate. The sideways light emission may be designed to be discontinuous. For instance, it may be useful to only have sideways illumination at the proximal end of the fiber located in the anus area. Having minimal or no loss at the distal area is beneficial to maximize the illumination power at the treatment area. The fiber may, for example, emit light substantially uniformly around the circumference of the fiber. The application of a sideways emitting light fiber may be useful in many other procedural instances, such as in endoscopic procedures, for e.g. locating a source of bleeding, and in stomach procedures. Fiber-cores could be made out of e.g. quartz or polymethyl-methacrylate.

As discussed above, it may be useful to adjust the frequency band of the emitted light to amplify the tissue in the treatment area. The frequency band may be adjusted in multiple ways, such as by using e.g., the balloon control 112, a separate controller that may be automatic or manual, etc. In a first example, a white light source, e.g. white light LEDs, may be used with a tunable optical bandpass filter to select an appropriate frequency band. The operating physician may have a control device for adjusting the frequency band of the filter. Using the bandpass filter allows for a flat spectral illumination within the chosen spectral range. In another example, several LEDs may be coupled into a single broadband fiber and the color of the fiber is modulated by adjusting the power of each individual LED. As each LED has a narrow spectral band, the combined spectral output is not a continuous flat spectral output. In a further embodiment, multiple frequency bands may be altered simultaneously by modifying a distribution of a spectrum in the visible light range.

In one embodiment, the inner member 104 of the balloon device 100 is the optical fiber 110 itself. FIGS. 3A-E show cross-sections of the optical fibers 110 with varying numbers of cores 128. Each of the cores 128 may be connected to a separate LED (each having a different frequency band) and each LED may be controlled according to the needs of the operating physician. In the single-core fiber, only one LED is used and thus only one frequency band may be used. In the three-core fiber, three different LEDs may be used, such as red, green and blue, and operated separately to provide greater control over the illumination of the optical fiber.

In another embodiment, the optical fiber 110 runs alongside the inner member 104. In this embodiment, the optical fiber 110 runs from the balloon control apparatus 112 through the outer tube 106. If the balloon 102, the inner member 104 and the outer tubing 106 are transparent, the light emitted from the fiber 110 illuminates not only the balloon 102 but also directly illuminates the treatment area proximal to the balloon, although this further illumination may not be as uniform as that provided by the illuminated balloon. In still another embodiment, the inner member 104 is hollow and the fiber 110 is inserted through the lumen of the inner member 104. In this embodiment, the fiber 110 may be a separate element from the rest of the balloon device 100 and only be introduced into the balloon device 100 just prior to or during the treatment procedure.

Figure 4A:
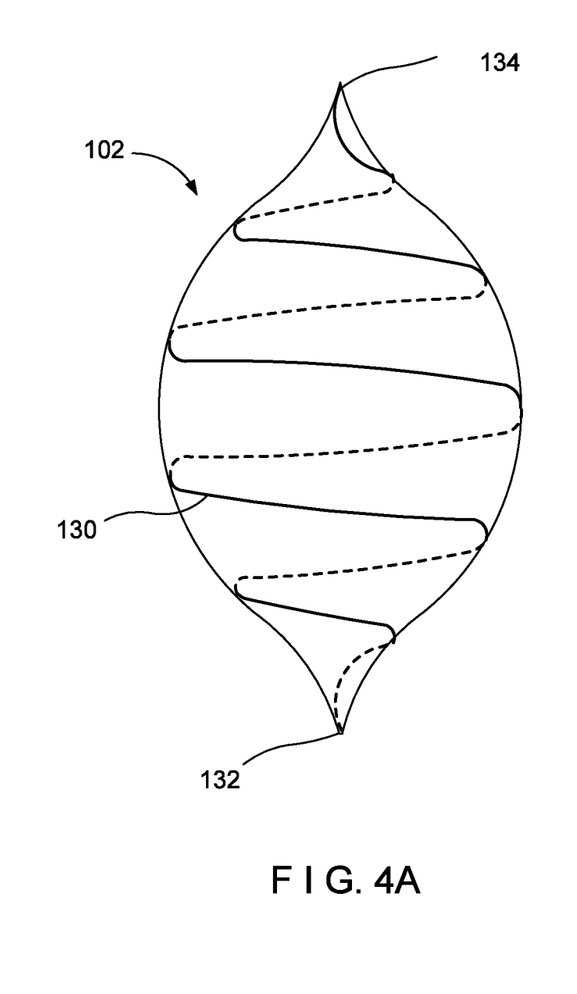
FIG. 4A shows a side view of the balloon device of FIG. 1 with the light-diffusing optical fiber as a light-emitting feature according to a first exemplary embodiment of the present disclosure.
Figure 4B:
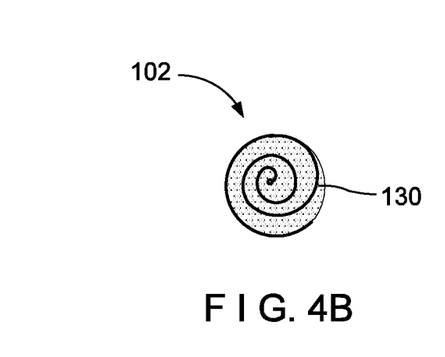
FIG. 4B shows a top view of the balloon device of FIG. 4A deflated.
Figure 4C:
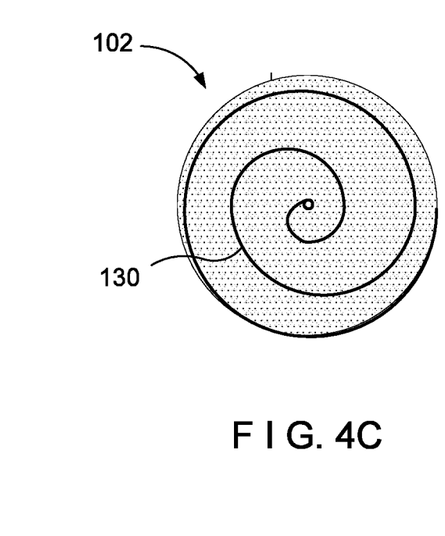
FIG. 4C shows a top view of the balloon device of FIG. 4A inflated.
Figure 5A:
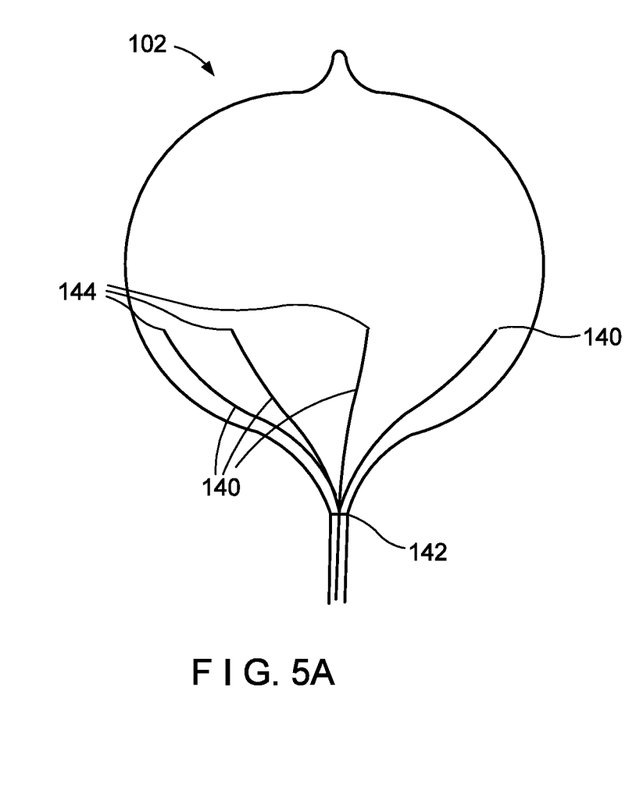
FIG. 5A shows a side view of the balloon device of FIG. 1 with the light-diffusing optical fiber as a light-emitting feature according to a second exemplary embodiment of the present disclosure.
Figure 5B:
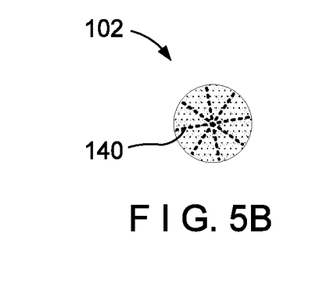
FIG. 5B shows a top view of the balloon device of FIG. 5A deflated.
Figure 5C:
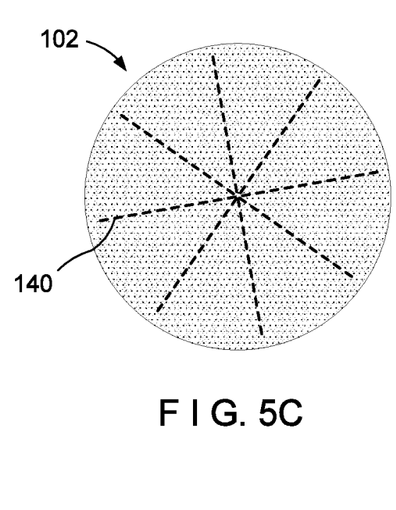
FIG. 5C shows a top view of the balloon device of FIG. 5A inflated.
Figure 5D:
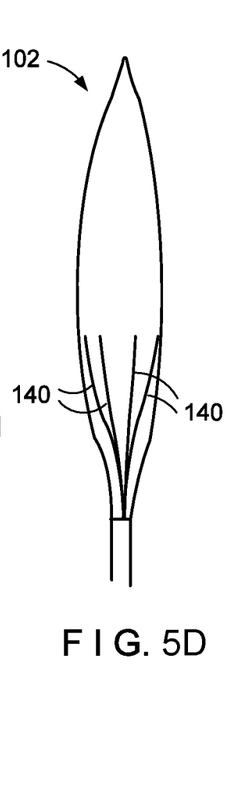
FIG. 5D shows a side view of the balloon device of FIG. 5A deflated.
Figures 6A, 6B, 6C:
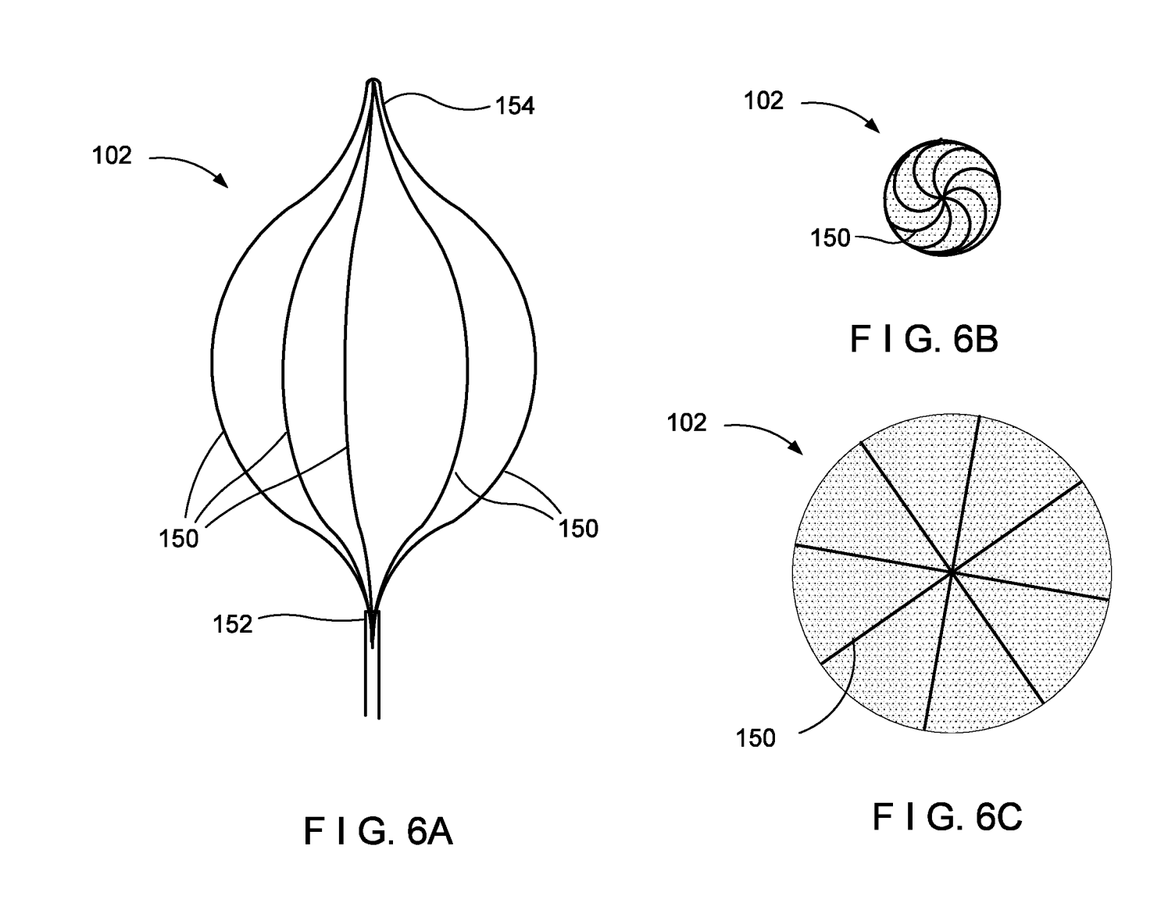
FIG. 6A shows a side view of the balloon device of FIG. 1 with the light-diffusing optical fiber as a light-emitting feature according to third exemplary embodiment of the present disclosure.
FIG. 6B shows a top view of the balloon device of FIG. 6A deflated.
FIG. 6C shows a top view of the balloon device of FIG. 6A inflated.

In yet another embodiment, the optical fiber 110 is embedded in the balloon. FIGS. 4-6 show the balloon device 100 of FIG. 1 with the light-diffusing optical fiber 110 as the light-emitting feature according to various exemplary embodiments of the present disclosure. No specific pattern is required to provide adequate illumination of the balloon 102, however, a pattern that lends itself to helping the fibers 110 stretch with the balloon 102 is preferred. In some embodiments, the balloon 102 may be semi-compliant or non-compliant, and its deflated state may have a predefined shape that accommodates the pattern of the fibers 110.

FIGS. 4A-C show an embodiment where an optical fiber 130 is embedded in a spiral pattern. The balloon 102 in this embodiment may be semi-compliant. The optical fiber 130 of this embodiment runs through the outer tube 106 shown in FIG. 1 or, alternatively, may be fully embedded in the balloon 102. In the present embodiment, the fiber 130 is fully embedded in the balloon 102 and runs from a first end 132 at the proximal end of the balloon 102 to a second end 134 at the distal end of the balloon 102. To aid in furling/unfurling, the fiber 130 is spiraled in a single direction, e.g., counterclockwise. The fiber 130 spirals in the single direction from a first end 132 to a second end 134. As may be seen in FIG. 4B, the spiral configuration allows for a deflated state where the fiber 130 spirals in a single direction. As the balloon 102 is inflated, the first portion and the third portion unfurl simultaneously in opposite directions. As may be seen in FIG. 4C in which the balloon 102 is unfurled.

Figure 8A:
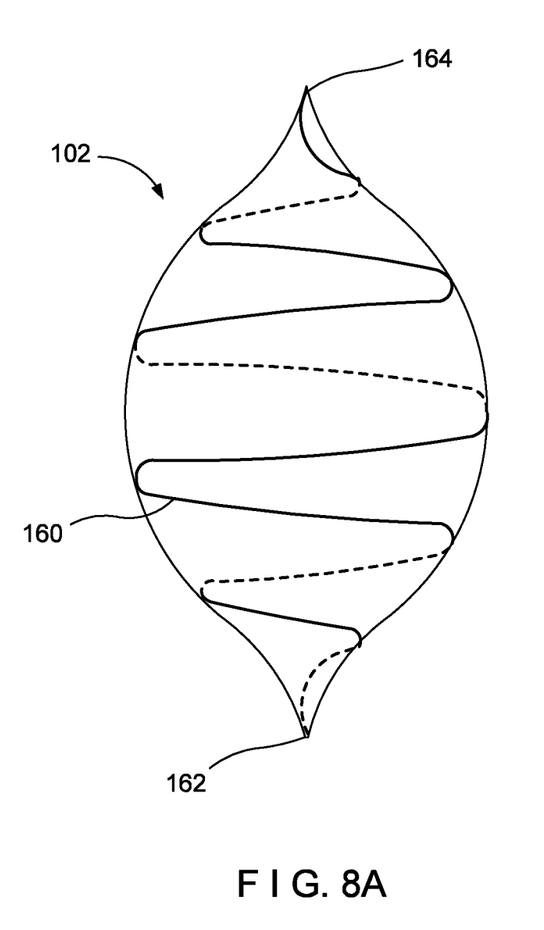
FIG. 8A shows a side view of the balloon device of FIG. 1 with the light-diffusing optical fiber as a light-emitting feature according to a fourth exemplary embodiment of the present disclosure.
Figure 8B:
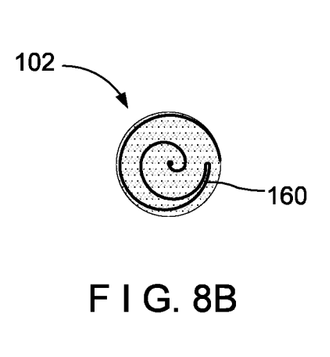
FIG. 8B shows a top view of the balloon device of FIG. 8A deflated.
Figure 8C:
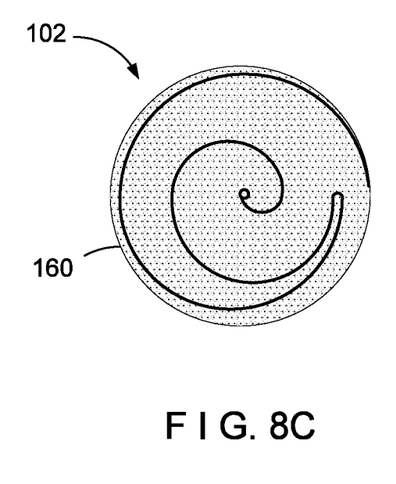
FIG. 8C shows a top view of the balloon device of FIG. 8A inflated.

FIGS. 8A-C show an embodiment where an optical fiber 160 is embedded in a spiral pattern. The balloon 102 in this embodiment may, for example, be semi-compliant. The optical fiber 160 of this embodiment runs through the outer tube 106 shown in FIG. 1 or, alternatively, may be fully embedded in the balloon 102. In the present embodiment, the fiber 160 is fully embedded in the balloon 102 and runs from a first end 162 at the proximal end of the balloon 102 to a second end 164 at the distal end of the balloon 102. To aid in furling/unfurling, a first portion of the fiber 160 beginning at the first end 162 is spiraled in a first direction, e.g., counterclockwise, a second portion of the fiber 160 in the middle is in a "switchback" configuration, where it transitions from the first direction (CCW) to a second direction, e.g., clockwise, and a third portion of the fiber 130 is spiraled in the second direction (CW), ending at the second end 164. As may be seen in FIG. 8B, the spiral/switchback configuration allows for a deflated state that is less stressful on the fiber 160 than a configuration where the spiral goes only in a single direction. As the balloon 102 is inflated, the first portion and the third portion unfurl simultaneously in opposite directions. As may be seen in FIG. 8C., the balloon 102 is unfurled. Although in the exemplary embodiment the fiber 160 has one switchback, as with ordinary skill in the arts will understand that the fiber 160 may have multiple switchbacks, and thus, have multiple portions of the fiber 160 unfurl simultaneously in opposite directions. Additionally, a further embodiment may have multiple spirals, with each of the multiple spirals having at least one switchback.

FIGS. 5A-D show an embodiment where a plurality of optical fibers 140 are embedded in an "umbrella-type" folding pattern. The balloon 102 in this embodiment may be non-compliant and have a plurality of optical fibers 140, e.g. eight optical fibers 140, running from a first end 142 at the proximal end of the balloon 102 to a second end 144 less than approximately halfway a distance between the proximal and distal end along the circumference of the balloon 102 when the balloon 102 is in the inflated state. Due to the non-compliant structure of the balloon 102, in the deflated state portions of the balloon are configured to collapse into folds. As may be seen in FIGS. 5B and 5D, the folded deflated portions of the balloon 102 are distal to the second ends 144 of the fibers 140, such that the fibers 140 are not folded when the balloon 102 is deflated. As may be seen in FIG. 5C., the balloon 102 is inflated.

FIGS. 6A-C show an embodiment where a plurality of optical fibers 150 are embedded in a "straight" pattern, each of the fibers 150 running from a first end 152 at the proximal end of the balloon 102 to a second end 154 at the distal end of the balloon 102. Similar to the embodiment shown in FIGS. 5A-D, the balloon 102 may be non-compliant and may have e.g. eight optical fibers 150. However, to avoid folding the fibers 150 when the balloon is deflated, the non-compliant structure of the balloon 102 is configured to collapse into a spiral pattern. In this way, the fibers 150 are not overly stressed when transitioning from the inflated to the deflated state.

Each of the optical fibers described in the previous embodiments has two longitudinal ends and at least one light source connected to one of the ends. However, a second light source may be used on the opposite end. The light source may be, e.g., a laser diode. However, other light sources may be used. Certain of the exemplary embodiments describe the fibers being embedded in the balloon, however, they may also be attached in different ways, such as bonding.

Figure 7:
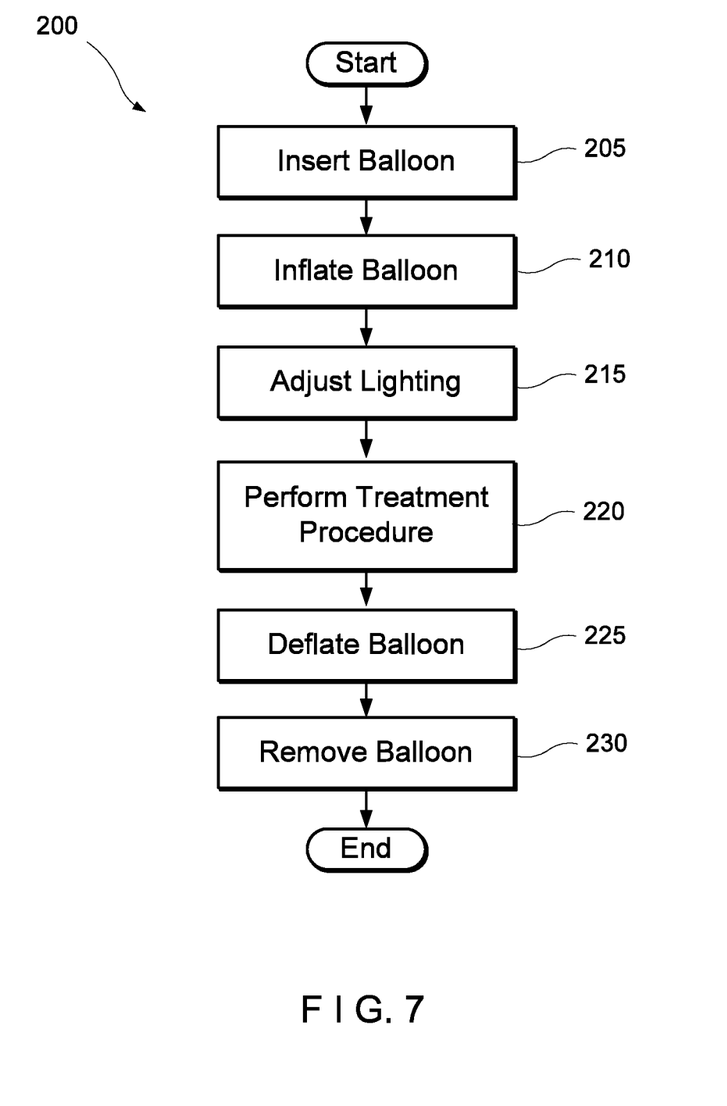
FIG. 7 shows a method for performing a hemorrhoid treatment procedure using the balloon device of FIG. 1.

FIG. 7 shows a method 200 for dilating the rectum and illuminating a treatment area for a hemorrhoid treatment procedure. The method 200 may be implemented with any of the aforementioned configurations of the balloon. In 205, the balloon device is inserted into the rectum. The light-emitting feature of the balloon may be actuated prior to insertion or, alternatively, may be actuated only after the balloon has been positioned within the body as desired. In 210, the balloon device is inflated to stretch the rectum and, indirectly, the anus.

Once the rectum has been expanded, the physician may inspect the hemorrhoid treatment area proximal to the balloon using the illumination from the balloon. In 215, the physician optionally adjusts the lighting provided by the balloon device. For example, the physician may determine that a different color or a greater/lesser light intensity would provide optimal lighting for the treatment procedure. The physician adjusts the lighting by, e.g., adjusting the voltage provided to the OLED foil or directly adjusting a color/intensity of the red-green-blue laser diode.

When the treatment conditions are optimal, the physician performs the treatment procedure in 220 using any known hemorrhoid treatment device and or method such as, for example, rubber band ligation, metal band ligation, snaring, etc. The physician may treat the hemorrhoidal tissue in any suitable manner using the increased treatment area and illumination provided by the balloon device.

In 225, after the treatment procedure has been completed, the balloon is deflated via the tube and, in 230, is removed from the body.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A device, comprising:
   a balloon configured for inflation with a light-diffusing fluid and configured, upon inflation, to expand a body lumen within which it is positioned; and
   a flexible light-emitting device attached to the balloon having a light-emitting side facing distally and radially inward toward the fluid so that, during a medical procedure, light emitted from the light-emitting side is diffused by the fluid and directed proximally to illuminate a treatment area within the body lumen proximal to the balloon.

2. The device of claim 1, further comprising:
   an inner member affixed to the balloon extending from a proximal end of the balloon to a distal end of the balloon; and
   an outer tube affixed to the proximal end of the balloon and extending to a fluid source.

3. The device of claim 2, wherein the inner member is a rod or a tube.

4. The device of claim 2, further comprising:
   an anchor plate comprising an affixation location for the outer tube, the anchor plate preventing the balloon from migrating during the medical procedure.

5. The device of claim 2, wherein the light-emitting device is an OLED foil with a non-light emitting side of the OLED foil being attached to an inner surface of the balloon.

6. The device of claim 5, wherein the OLED foil has power terminals and wiring extending from the power terminals through the inner member to a power source.

7. The device of claim 1, wherein the light-emitting device comprises at least one optical fiber embedded in a surface of the balloon.

8. The device of claim 1, wherein a distribution of a spectrum in the visible light range is modifiable to adjust a frequency and an intensity of the light emitted from the light-emitting device.

9. The device of claim 1, wherein the balloon is one of non-compliant or semi-compliant.

10. A device, comprising:
    a balloon configured for inflation with a light-diffusing fluid and configured, upon inflation, to expand a body lumen within which it is positioned; and
    a light-emitting device attached to the balloon and emitting light directed so that, when the device is in a desired position within a living body, the light passes through the light-diffusing fluid toward a treatment area within the body lumen proximal to the balloon, wherein the light-emitting device is interior to the balloon and extends from a proximal end of the balloon to a distal end of the balloon, the light-emitting device emitting light radially outward through the light-diffusing fluid.

11. The device of claim 10, further comprising:
an inner tube attached to the balloon and extending from a proximal end of the balloon to a distal end of the balloon,
wherein the light-emitting device is in the interior of the inner tube.

12. The device of claim 11, wherein the light-emitting device is an optical fiber.

13. The device of claim 10, wherein the light-emitting device is an OLED foil.

14. The device of claim 10, wherein a distribution of a spectrum in the visible light range is modifiable to adjust a frequency and an intensity of the light emitted from the light-emitting device.

15. A method, comprising:
inserting a device into a body lumen of a living body, the device comprising a balloon inflatable with a light-diffusing fluid and a flexible light-emitting device having a non-light emitting side coupled to the balloon and having a light-emitting side facing radially inward toward the fluid; and
inflating the balloon with the light-diffusing fluid so that light emitted from the light-emitting side is diffused by the fluid and illuminates to illuminate a treatment area within the body lumen proximal to the balloon.

16. The method of claim 15, wherein the light-emitting device is an OLED foil.

17. The method of claim 16, wherein the OLED foil has power terminals and wiring extending from the power terminals through an inner member to a power source.

18. The method of claim 15, wherein the light-emitting device comprises at least one optical fiber embedded in a surface of the balloon.

19. The method of claim 15, wherein a distribution of a spectrum in the visible light range is modifiable to adjust a frequency and an intensity of the light emitted from the light-emitting device.

* * * * *